US005769891A

United States Patent [19]
Clayton

[11] Patent Number: 5,769,891
[45] Date of Patent: Jun. 23, 1998

[54] PROSTHESIS FOR ALLEVIATING TMJ DISCOMFORT

[75] Inventor: Lawrence G. Clayton, 5330 Parliament Pl., Rockford, Ill. 61107

[73] Assignee: Lawrence G. Clayton, Rockford, Ill.

[21] Appl. No.: 874,819

[22] Filed: Jun. 13, 1997

[51] Int. Cl.[6] ........................ A61F 2/18
[52] U.S. Cl. ........................ 623/10; 623/12
[58] Field of Search ........................ 623/10, 11, 12

[56] References Cited

U.S. PATENT DOCUMENTS 4,094,303 6/1978 Johnston ........................ 623/10 X
5,480,433 1/1996 Nadol, Jr. ........................ 623/12 X
5,553,152 9/1996 Newton ........................ 623/10 X
5,645,584 7/1997 Suyama ........................ 623/10

*Primary Examiner*—Mary Beth Jones
*Attorney, Agent, or Firm*—Leydig, Voit & Mayer Ltd

[57] ABSTRACT

A prosthesis for insertion in an ear to reduce pain resulting from TMJ disorders. The ear insert conforms to the shape of the ear canal when the jaw is in an open position. The ear insert supports the TMJ and associated secondary musculature to reduce strain in the TMJ area, including the muscles, ligaments, nerves, and the temporo-mandibular joint itself. The insert is hollow on the inside to permit hearing and is made of a rigid material which retains the shape of the ear canal. A method for forming the ear insert includes forming a mold of the ear canal when the jaw is in the open position. The mold is then used to form the ear insert.

13 Claims, 1 Drawing Sheet

PROSTHESIS FOR ALLEVIATING TMJ DISCOMFORT

FIELD OF THE INVENTION

The present invention generally relates to medical devices and, more particularly relates to devices for relieving temporo-mandibular joint discomfort.

BACKGROUND OF THE INVENTION

Many people suffer from pain in a joint located between the skull and the jaw. The joint is formed between the temporal bone of the skull and the mandible, and is commonly known as the temporo-mandibular joint or "TMJ". The human body actually has two temporo-mandibular joints, one located on each side of the jaw in front of each ear. The TMJs move every time a person chews, talks, or even swallows.

In greater detail, the TMJ is a paired joint articulating the mandibular condyle, articulator disc, and squamous portion of the temporal bone, and is capable of glide and hinge movements. Specifically, the TMJ is formed by the mandibular condyle fitting into the mandibular fossa of the temporal bone. A separation of these two bones is accomplished by the articulator disc which is composed of dense fibrous connective tissue. Ligaments attach the disc to the condyle, permitting rotational movement of the disc during mouth opening and closure. Each TMJ has an articulator disc of primarily cartilage material located between the condyle area and the temporal bone. The disc moves within the joint during opening and closure of the jaw and, when displaced, strains the jaw muscles and causes muscle pain or fatigue around the jaw. In addition, disc displacement often causes a painful clicking in the TMJ during certain jaw movements as the disc moves between normal and displaced positions. A number of other symptoms may occur as a result of a strained disc, including TMJ lock, shoulder, neck, and back pain, and headaches.

Unfortunately, conventional methods of treating temporomandibular joint disorders can be costly, physically cumbersome, or involve invasive and irreversible treatment. Some conservative methods for treating TMJ discomfort include the use of an intra-oral splint, medication, and life style changes. One type of intra-oral splint is a stabilization apparatus which is used to help alter the posture of the mandible to a more open, relaxed, resting position. Another type of intra-oral splint is an anterior positioning apparatus. The anterior positioning apparatus attempts to decrease the compression load on the joint and alter the structural condyle disc relation. Both types of splints, however, cannot be used full time without risking displacement of teeth. Treatment by medication often involves the use of addictive drugs and/or anti-depressants and therefore can lead to misuse and abuse. In addition, medications often produce adverse side effects in the patient. Other conservative methods include chiropractic or physical therapy. Unfortunately, these methods require extensive time commitments and physical exertion by the patient.

More aggressive treatment of TMJ discomfort includes orthodontic treatment such as grinding down of teeth and various types of surgery. Orthodontic treatments, however, merely indirectly address TMJ pain by adjusting the dental articulation and overall bite of the patient. Furthermore, orthodontic approaches are invasive, irreversible, and expensive.

SUMMARY OF THE INVENTION

In view of the foregoing, it is a general aim of the present invention to provide a device for alleviating TMJ discomfort which is easy to use, inexpensive, and relatively non-invasive.

In that regard, an object of the present invention is to provide a device for treating TMJ disorders which acts directly on the TMJ and associated ligament and muscle structures to reduce stress and loads placed on the articulator disc located between the the temporal bone and the mandible, as well as supportive muscles and ligaments near the TMJ.

More specifically, it is an object of the present invention to provide an ear insert which supports the TMJ structure to reduce loads and stresses associated with the masticatory musculature, the temporo-mandibular joint, and associated structures, thereby reducing TMJ discomfort.

It is also an object of the present invention to provide a method for forming a prosthesis so that the prosthesis fits in an ear canal and relieves TMJ discomfort.

It is, therefore, a feature of the present invention to provide an ear insert made of relatively rigid material shaped for insertion in the ear canal of a patient to a certain depth. The ear insert is formed to closely conform to the shape of the ear canal when the jaw is in an unoccluded or open position. When the device is placed in each ear and the jaw is subsequently closed, the ear insert influences the positioning of the jaw in relation to the temporal bone to thereby relieve strain on the TMJ.

It is also a feature of the present invention to provide a method for forming an ear insert having the proper anatomical shape. Mold material is injected into an ear canal when the TMJ is in an unoccluded position. An ear insert formed from the impression, when inserted in the ear canal, reshapes the ear canal to correspond to the ear canal contour associated with the unoccluded TMJ position.

These and other objects and advantages of the invention will become more apparent from the following detailed description when taken in conjunction with the accompanying drawings.

Figure 1:
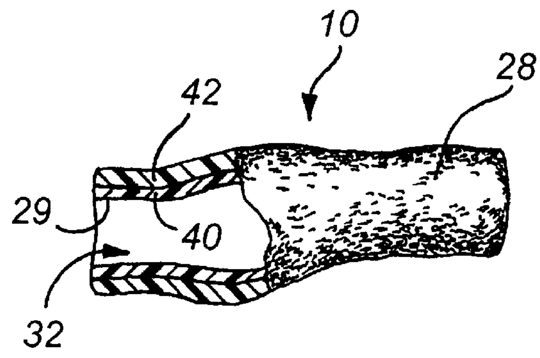
FIG. 1 is a partial section side view of a prosthesis in accordance with the present invention.

While the invention is susceptible of various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention as defined by the appended claims.

DETAILED DESCRIPTION OF THE PREFERRED EMBODIMENT

For purpose of illustration, the invention is shown in FIG. 1 as embodied in a prosthesis 10 adapted for insertion into, and to generally correspond to the shape of, an ear canal 12. In practicing the invention, the ear insert 10 influences the relationship between the temporal bone 14 and the mandible 16 in each temporo-mandibular joint 18, thereby relieving pain inducing stress in the TMJ and related muscles, ligaments, and nerves, as will be described with further detail herein.

Figure 3:
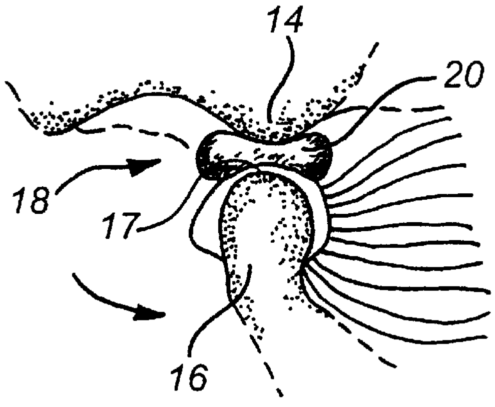
FIG. 3 is a side view of a TMJ in an unoccluded position showing a disc in the normal position.
Figure 4:
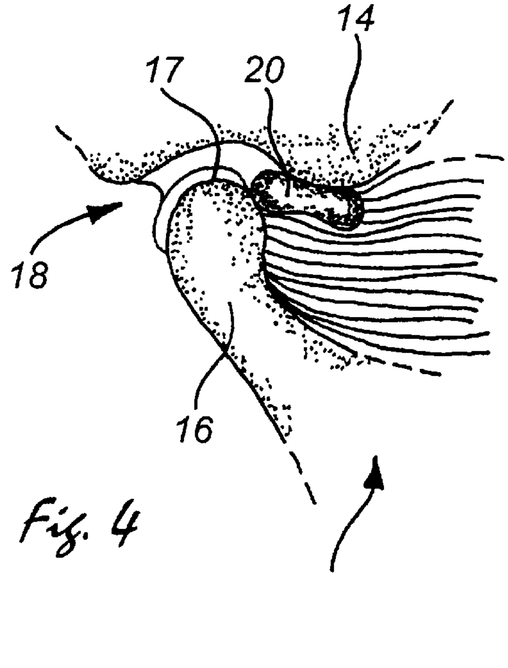
FIG. 4 is a side view of a TMJ in the closed position showing a disc in the displaced position.

One source of TMJ discomfort is a dislocated disc 20. As shown in FIG. 3, when the jaw or mandible 16 is in an open or unoccluded position, the disc 20 is usually in a normal, unstrained position between the temporal bone 14 and a condyle surface 17 of the mandible. As is often the case with a person experiencing TMJ discomfort, the disc 20 slips to a displaced position when the mandible 16 is subsequently closed, as illustrated in FIG. 4. The displacement of the disc 20 is often indicated by a clicking or popping noise as the jaw 16 moves between open and closed positions. In the displaced position, the disc is no longer between the condyle surface 17 and the temporal bone 14, and the disc 20 and ligaments attached to the disc become strained. Strain on these members stresses the surrounding muscles, which may ultimately result in face, neck, and back pain.

To treat TMJ discomfort arising from a displaced disc 20, and in accordance with the present invention, the intra-aural prosthesis 10 is provided for reducing stresses and loads on the disc 20. The ear insert 10 reshapes the ear canal and provides a rigid structure which helps align the TMJ 18 and associated muscle and ligament structures so that the TMJ has normal rotational movement between the condyle surface 17 and inferior surface of the articulator disc 20. Strain or compression on the disc 20 is therefore reduced, thereby alleviating pain in the TMJ and associated structures.

It should be noted that a dislocated disc is only one cause of TMJ discomfort and that there are many other sources of such pain. Nerves, ligaments, and muscle groups (such as the masticatory musculature) are located proximal to the TMJ, and improper loading, strain, or alignment of these members provide potential sources of TMJ pain. Rather than being limited to disc dislocation situations, as outlined above, the present invention addresses misalignment and stress in the TMJ and related structures by supporting these structures for normal rotational movement between the condyle 17 and disc 20.

Figure 2:
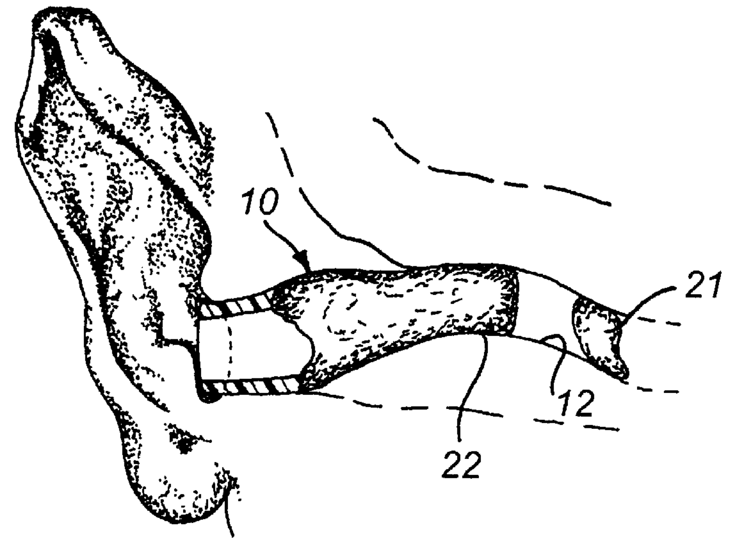
FIG. 2 is a partial section side view of the prosthesis of FIG. 1 inserted into an ear canal.

Turning to the structure of the ear insert 10, it will be appreciated that the insert conforms to the contours of an ear canal 12 (FIG. 2). The ear canal 12 forms a generally cylindrical path leading to the tympanic membrane 21. A bend in the ear canal known as the isthmus 22 is located approximately 20–23 millimeters from the outside of an adult ear, and is located in close proximity to the TMJ 18. As shown in FIG. 1, the ear insert 10 has an outside surface 28 molded to conform to the ear canal 12. The ear insert 10 has a generally cylindrical inner core 29. The outside surface 28 is shaped to engage the surface of the ear canal 12. The specific diameter of the ear insert 10 depends on the precise size of the patient's ear canal, but is generally ranges around 7–9 millimeters. The insert 10 is preferably 20–22 millimeters long so that it engages the isthmus 22 of the ear canal.

As best shown in FIGS. 1 and 2, the ear insert 10 preferably has a hollow center 32 which allows the patient to hear while wearing the ear inserts 10. In an alternative embodiment, ear insert 10 need not be completely hollow, but could be formed from a sufficiently acoustically conductive material which enables the patient to hear. In still another embodiment, for example an ear insert for use at night while sleeping, it is desirable to reduce the amount of noise which the patient can hear. In this embodiment, the ear insert 10 has a solid construction formed of material which absorbs or otherwise reduces audible noise levels.

The ear insert 10 is made from moldable material which cures to form a rigid structure. In the preferred embodiment, the ear insert 10 is made of two layers. The first or interior surface 40 is made of hard material such as clear acrylic, while the second or exterior surface 42 is made of relatively soft material such as PVC or silicone, as shown in FIG. 1. It will be appreciated that in the two-layer ear insert 10, the interior surface 40 maintains the shape of the ear canal 12 while the exterior surface 42 improves the comfort of the insert. In an alternative embodiment, the ear insert 10 comprises a single layer of rigid yet comfortable material such as hard acrylic.

In accordance with a significant aspect of the present invention, the ear insert 10 conforms to the shape of the ear canal 12 when the mandible 16 is in the unoccluded position. In order to accomplish this, the present invention further provides a novel method for fabricating the ear insert 10. The method includes the step of forming a mold of the ear canal 12 using one of two methods. The first method uses a powder and oil catalyst and the second method uses a silicone mixture to form a mold of the ear canal 12. Significantly, the ear canal impression is formed with the mandible 16 in an unoccluded position. The impression is then used to form the ear insert 10. It will therefore be appreciated that when placed inside the ear canal 12, the ear insert 10 manipulates the shape of the ear canal so that it corresponds to the ear canal shape associated with an open jaw.

The required positioning of the jaw 16 for the above method can be carried out by simply placing an object between the teeth of a patient to space the jaw during the molding step. It has been found that a gap of about 15–17 millimeters between upper and lower teeth of the patient is adequate. A simple tool for maintaining this gap is tongue depressor placed between the patient's teeth so that the width of the depressor is aligned vertically. It is to be understood, however, that a tongue depressor is but one example of such a span tool, and that a variety of other objects can be employed with similar efficacy.

In an alternative embodiment, the ear insert 10 may be formed in standard sizes adapted for universal fit. In this embodiment, the ear insert 10 is generally cylindrical and has pre-determined contour, shape, and length for insertion into a typical ear. The ear insert 10 is pre-formed using conventional fabrication techniques rather than being formed from an ear mold. Accordingly, the ear insert 10 is sized to have a diameter in a typical range, such as 6–9 millimeters. The ear insert 10 also has a length adapted to reach the isthmus 22 of a typical ear, such as between 20–22 millimeters. In addition, the ear insert 10 is shaped to match the typical contour of an ear canal 12. By forming the ear insert 10 according to the criteria listed above, the ear insert 10 is pre-fabricated, and does not require the formation and use of an ear mold to form the insert. This embodiment further contemplates providing a set of differently sized standard ear inserts, such as small, medium, and large. Each size is formed having a length, diameter, and shape which is adapted to engage the isthmus 22 of a typical ear of corresponding small, medium, or large size. Under this embodiment, the ear inserts 10 may be provided in pre-determined standard sizes.

It will therefore be appreciated that the ear insert 10 of the present invention alleviates TMJ discomfort by supporting the TMJ 18 and associated muscles, nerves, and ligaments for proper rotation of the mandible between open and closed positions. Returning to the specific example of a dislocated disc, the normal and displaced positions of the disc 20 are illustrated in FIGS. 4 and 5, respectively. The ear insert 10 is formed to correspond to the shape of the ear canal 12 when the jaw 16 is unoccluded and the disc 20 is in the normal position. When the jaw 16 is subsequently closed, the ear insert 10 maintains the positioning of the jaw so that the disc 20 is not displaced. Accordingly, the present invention advantageously utilizes a natural body orifice to reposition the mandible 16 without requiring surgery or other painful and invasive techniques. As noted above, the example of a dislocated disc is merely illustrative of a TMJ condition addressed by the present device and is in no means meant to limit the scope of the present invention. Accordingly, it will be appreciated that the present device addresses stresses and misalignments in not only the disc but also any muscles, ligaments, and nerves associated with the TMJ.

From the foregoing it will be appreciated that the present invention provides a prosthesis for treating TMJ discomfort. The prosthesis is in the form of an ear insert which is shaped to conform to the surface of an ear canal when the mandible is open. The ear insert is sufficiently long to engage the isthmus of the ear canal. The ear insert supports the TMJ for normal rotation between the mandible and the temporal bone to reduce strain (and discomfort caused by strain) in the TMJ and associated muscles, ligaments, and nerves.

What is claimed is:

1. A prosthesis adapted to be inserted into an ear canal having an isthmus for treating discomfort in a joint between a mandible and a corresponding temporal bone, the joint having a disc located between the mandible and the temporal bone and associated musculature, the prosthesis having a generally cylindrical core with an exterior surface shaped to substantially conform to a contour of the portion of the ear canal which extends approximately between the entrance to the ear canal and the isthmus, the prosthesis, when inserted, adapted to support the joint and associated musculature for rotational movement of the mandible about the disc, thereby reducing discomfort in the joint.

2. The prosthesis of claim 1 in which the prosthesis aligns the disc in a normal position between the mandible and the temporal bone by repositioning the mandible with respect to the temporal bone.

3. The prosthesis of claim 1 in which the associated musculature includes muscles and ligaments located near the joint, the prosthesis supporting proper alignment of the muscles and ligaments to reduce strain, thereby alleviating joint discomfort.

4. The prosthesis of claim 1 in which the exterior surface has a length, the length sufficient to allow the prosthesis to engage the isthmus of the ear canal.

5. The prosthesis of claim 1 in which the prosthesis is made of hard acrylic.

6. The prosthesis of claim 1 including an interior surface made of hard material, the exterior surface comprising a relatively softer material.

7. The prosthesis of claim 6 in which the interior surface is clear acrylic and the exterior surface is PVC.

8. The prosthesis of claim 1 having a hollow center.

9. The prosthesis of claim 1 in which the exterior surface conforms to the contour of the ear canal when the mandible is in an unoccluded position.

10. A prosthesis adapted to be inserted into a typical ear canal having an isthmus for treating discomfort in a joint between a mandible and a corresponding temporal bone, the joint having a disc located between the mandible and the temporal bone and associated musculature, the prosthesis having a generally cylindrical core with an exterior surface, the exterior surface having a length and diameter shaped to substantially conform to a contour of the portion of the ear canal which extends approximately between the entrance to the ear canal and the isthmus when the mandible is in an unoccluded position, the prosthesis, when inserted, adapted to support the joint and associated musculature for rotational movement of the mandible about the disc, thereby reducing discomfort in the joint.

11. The prosthesis of claim 10 in which the length and diameter of the exterior surface are sufficient to allow the prosthesis to engage the isthmus of the ear canal.

12. The prosthesis of claim 11 in which the length of the exterior surface is approximately 20–22 millimeters.

13. The prosthesis of claim 12 in which the diameter of the exterior surface is approximately 6–9 millimeters.

* * * * *